United States Patent [19]
Okayama et al.

[11] Patent Number: 5,654,004
[45] Date of Patent: Aug. 5, 1997

[54] ORAL PHARMACEUTICAL PREPARATION RELEASABLE IN THE LOWER DIGESTIVE TRACT

[75] Inventors: Minenobu Okayama; Masaru Nakanishi, both of Tsukuba, Japan

[73] Assignee: Hisamitsu Pharmaceutical Co., Inc., Tosu, Japan

[21] Appl. No.: 432,202

[22] PCT Filed: Nov. 5, 1993

[86] PCT No.: PCT/JP93/01608
§ 371 Date: May 5, 1995
§ 102(e) Date: May 5, 1995

[87] PCT Pub. No.: WO94/10983
PCT Pub. Date: May 26, 1994

[30] Foreign Application Priority Data

Nov. 6, 1992 [JP] Japan ................... 4-322478

[51] Int. Cl.$^6$ ................... A61K 9/32; A61K 9/50
[52] U.S. Cl. ................... 424/479; 424/480; 424/482; 424/483; 424/493; 424/494; 424/497
[58] Field of Search ................... 424/483, 482, 424/480, 493, 494, 497, 479

[56] References Cited

U.S. PATENT DOCUMENTS

| | | |
|---|---|---|
| 4,432,966 | 2/1984 | Zeitoun et al. . |
| 4,775,536 | 10/1988 | Patell .................... 424/482 |
| 4,780,318 | 10/1988 | Appelgren et al. ...... 424/482 |
| 4,780,322 | 10/1988 | Martani et al. ........ 424/78.14 |
| 4,996,047 | 2/1991 | Kelleher et al. ....... 424/78.15 |
| 5,296,236 | 3/1994 | Santus et al. ............ 424/484 |

FOREIGN PATENT DOCUMENTS

| | | |
|---|---|---|
| 2246037 | 4/1974 | Germany . |
| 2066070 | 7/1981 | United Kingdom . |

*Primary Examiner*—Thurman K. Page
*Attorney, Agent, or Firm*—Bucknam and Archer

[57] ABSTRACT

An oral pharmaceutical preparation releasable in the lower digestive tract, characterized by having a double-coated structure wherein a solid drug having a core containing an active ingredient is covered with both an inner coat made of a cationic polymer and an outer coat made of an anionic polymer.

7 Claims, 9 Drawing Sheets

ORAL PHARMACEUTICAL PREPARATION RELEASABLE IN THE LOWER DIGESTIVE TRACT

This application is a 35 USC 371 of PCT/JP93/01608 filed Nov. 5, 1993.

TECHNICAL FIELD

The present invention relates to an oral pharmaceutical preparation which is releasable in the lower digestive tract. In particular, the present invention relates to a pharmaceutical preparation for oral administration which passes through the stomach without being affected by gastric juice, does not undergo any change in the small intestine, and begins to disintegrate for the first time when it arrives at the large intestine to release the active ingredient, which is absorbed therein.

BACKGROUND ART

The pharmaceutical preparations for oral administration according to the prior art begin to disintegrate or dissolve before the arrival at the large intestine. Therefore, it has been a practice in the prior art to employ an intravenous, intranasal or rectal administration method in the administration of an active substance which is expected to exhibit a local action on the large intestine or is decomposed by the lyase present in the small intestine.

However, an oral pharmaceutical preparation has the following advantages. Namely, if an oral pharmaceutical preparation releases a pharmacologically active substance selectively in the large intestine, the concentration of the active substance at the release site can be increased to give a more effective local action than that of the preparation according to the prior art. Further, if a pharmacologically active protein or peptide which is decomposed in the small intestine loses its activity and is released selectively in the large intestine, the protein or peptide will be able to be absorbed in the large intestine wherein the protease activity is poor. Owing to the above advantages, it is apparent that an oral pharmaceutical preparation is a dosage form far more useful than injection or suppository.

For the reason described above, many attempts have recently been made to develop oral pharmaceutical preparations targeting the large intestine.

For example, there have been reported an oral preparation targeting the large intestine, which is prepared by combining a polymer soluble only at a pH of 5.5 or above with an insoluble polymer (EP40590); a solid oral preparation coated with a suitable amount of an anionic polymer soluble at a pH of 7.0 or above (trade name: Eudragit S, a product of RÖHM) (WO83/00435); an oral preparation coated with a mixture comprising an anionic polymer soluble at a pH of 7.0 or above (trade name: Eudragit S or L, a product of RÖHM) and a methacrylate copolymer difficultly soluble in water (trade name: Eudragit RS, a product of RÖHM) at a suitable ratio (EP225189); an osmotic-pump preparation coated with an enteric polymer (BE903502); a colon-reaching oral preparation covered with an inner coat soluble at a pH of 7.0 or above, an intermediate coat made of a gelatinized polymer, and a acid-resistant outer coat soluble at a pH of 5.5 or above (Japanese Patent Publication No. 501411/1992); and so forth.

All of these preparations are characterized in that a drug is released by a pH increase in the intestinal tract, and they are each prepared by applying a proper amount of an anionic polymer or by adding or applying an insoluble polymer to prevent the drug from being released during its residence in the small intestine.

Meanwhile, a recent study on humans (D. F. Evans, Gut, 1988, vol.29, p.1035) reported that the pH of the intermediate and lower parts of the small intestine ranges from 7.4 to 7.5 (standard deviation: 0.4 to 0.5), while the average pH rapidly drops to 6.4 (standard deviation: 0.4) in the upper part of the large intestine and gradually increases to reach 7.0 (standard deviation: 0.7) in the lower part of the large intestine.

However, all of the above oral preparations releasable in the large intestine according to the prior art are coated with a polymer soluble or swelling at a pH of 7.0 or above, on the assumption that the pH in the colon or large intestine is 7.0 or above. The inventors of the present invention have also made intensive studies on this respect and have found that the pH of cecal contents of a rat or rabbit is below the range of 6.4 to 5.5 owing to the organic acids generated by enteric bacteria. This result agrees with that disclosed in the above literature on humans. Accordingly, the inventors of the present invention have started studies to develop an oral pharmaceutical preparation from which a drug is released in the lower digestive tract (large intestine) by a pH change to below the range of 7.0 to 5.5.

Further, WO90/13286 discloses an oral preparation comprising a core containing a basis and a filler, a first layer which covers the core and is composed of an enteric component, a second layer which covers the first layer and is composed of a nonenteric component, and a third layer which covers the second layer and is composed of an enteric component. In this oral preparation, the second layer, which is composed of a cationic polymer, is covered with the third layer to regulate the release of a drug, so that it is very difficult to regulate the preparation so as to release a drug specifically in the large intestine. Further, since the core always contains an acidic substance, the second layer is liable to be dissolved in the small intestine to release a drug prior to the arrival at the large intestine.

The coat according to the prior art has such a property that the dissolution or swelling thereof proceeds before the arrival of the preparation at the large intestine. Therefore, the preparation of the prior art has a disadvantage that when the actual residence time in the small intestine, which has a great physiological influence, is shorter than the one assumed in the dosage form design, the preparation is discharged as such, while when the actual residence time is longer than the assumed one, the release of a drug has been completed before the arrival at the target site.

DISCLOSURE OF THE INVENTION

The present invention aims at solving the above problem of the prior art to develop an oral pharmaceutical preparation which passes through the stomach without being affected by gastric juice, does not undergo any change in the small intestine, and begins to disintegrated for the first time when it arrives at the large intestine to release the active ingredient, which is absorbed therein.

The oral pharmaceutical preparation releasable in the lower digestive tract according to the present invention is characterized by having a double-coated structure wherein a solid drug having a core containing an active ingredient is covered with both an inner coat made of a cationic polymer and an outer coat made of an anionic polymer.

Namely, the present invention relates to a novel oral pharmaceutical preparation which comprises a solid drug having a core containing a therapeutically active ingredient which is releasable in the lower digestive tract, and the following coats (①) and (②):

coat (①): inner coat which contains a suitable plasticizer or binding inhibitor and is made of a cationic polymer soluble or swelling at a pH of 6.0 or below, and coat (②): outer coat made of an anionic polymer soluble at a pH of 5.5 or above.

The solid drug having the core is made of a therapeutically active ingredient alone or a mixture thereof with a filler, binder, disintegrator and/or sorbefacient.

Examples of the filler include lactose, crystalline cellulose, crystalline cellulose sodium carboxymethylcellulose, wheat starch, and magnesium stearate.

Examples of the binder include crystalline cellulose, pullulan, acacia, sodium alginate, polyvinyl pyrrolidone and macrogol.

Examples of the disintegrator include ordinary inert substances for pharmaceutical preparations, such as carboxymethylcellulose, calcium carboxylmethylcellulose, hydroxypropylcellulose, hydroxypropylstarch, starch and sodium alginate.

Further, a sorbefacient may be used in the preparation of the solid drug to accelerate the absorption of the active ingredient, and examples of such a sorbefacient include sugar ester, sucrose esters of fatty acid, glycyllysinate salts, glycyrrhetinic acid, dipotassium glycyrrhizinate, bile acid, glycerol esters of fatty acid, 1-[(2-(decylthio)ethyl] azacyclopentan-2-one, adipic acid, basic amino acids, polyethylene glycol and sodium caprate.

The solid drug may be encapsulated with gelatin or may be granulated or tabletted.

The therapeutically active ingredient to be contained in the solid drug is not particularly limited but may be any substance which exhibits its effect when released in the lower digestive tract. Examples of the therapeutically active ingredient include peptides, proteins, anti-inflammatory agents, antineoplastic agents, antibiotics, chemotherapeutics, ulcerative colitis remedy, irritable colitis remedy (choline blocker), and constipation remedy. Specific examples of the therapeutically active ingredient include somatostatin, insulin, calcitonin, vasopressin, gastrin, EGF (epidermal growth factor), α-hANP (α-human atrial natriuretic peptide), enkephalin, endorphin, GM-CSF (granulocyte macrophage colony-stimulating factor), G-CSF (granulocyte colony-stimulating factor), human growth hormone, glucagon, t-PA (tissue plasminogen activator), TNF (tumor necrosis factor), TCGF (T cell growth factor), ACTH (adrenocorticotrophic hormone), interleukins, interferon, EPO (erythropoietin), urokinase, neocarcinostatin, bradykinin, immunoglobulin and its digestion product, various allergens and their digestion products, ketoprofen, ibuprofen, diclofenac, indometacin, ketrolac, fenbufen, loxoprofen, tenidap, piroxicam, tenoxicam, salazosulfapyridine, pipethanate hydrochloride, mepenzolate bromide, and sennosides A and B.

The cationic polymer which is soluble or swelling at a pH of 6.0 or below and is used in the formation of the inner coat is an aminoalkyl methacrylate copolymer (a copolymer comprising methyl methacrylate, butyl methacrylate and dimethylaminoethyl methacrylate, trade name: Eudragit E, a product of RÖHM) or a polyvinyl acetal diethylaminoacetate (trade name: AEA, a product of Sankyo). The inner coat is formed by applying 1 to 40% by weight (based on the solid drug) of the above polymer to the solid drug in a film thickness of 10 to 300 μm, by which the resulting preparation is regulated so as to release the active ingredient therefrom speedily when the pH condition of 6.0 or below continues.

It is preferable that a suitable plasticizer be used in the formation of the inner coat to make the coat smooth. The plasticizer includes triacetin, citrate ester and polyethylene glycol. The binding inhibitor includes talc, titanium oxide, calcium phosphate, hydrophobic light anhydrous silicic acid, and so forth.

The outer coat is made of an anionic polymer which is easily soluble at a pH of 5.5 or above. Examples of the anionic polymer usable in the present invention include methacrylic acid copolymer L (a copolymer comprising methacrylic acid and methyl methacrylate, trade name: Eudragit L100, a product of RÖHM), methacrylic acid copolymer S (a copolymer comprising methacrylic acid and methyl methacrylate, trade name: Eudragit S, a product of RÖHM), hydroxypropylcellulose, hydroxyethylcellulose phthalate, polyvinyl acetate phthalate, cellulose acetate phthalate, and cellulose acetate tetrahydrophthalate. The anionic polymer is applied in an amount of 1 to 40% by weight based on the solid drug.

BEST MODE FOR CARRYING OUT THE INVENTION

Figure 1:
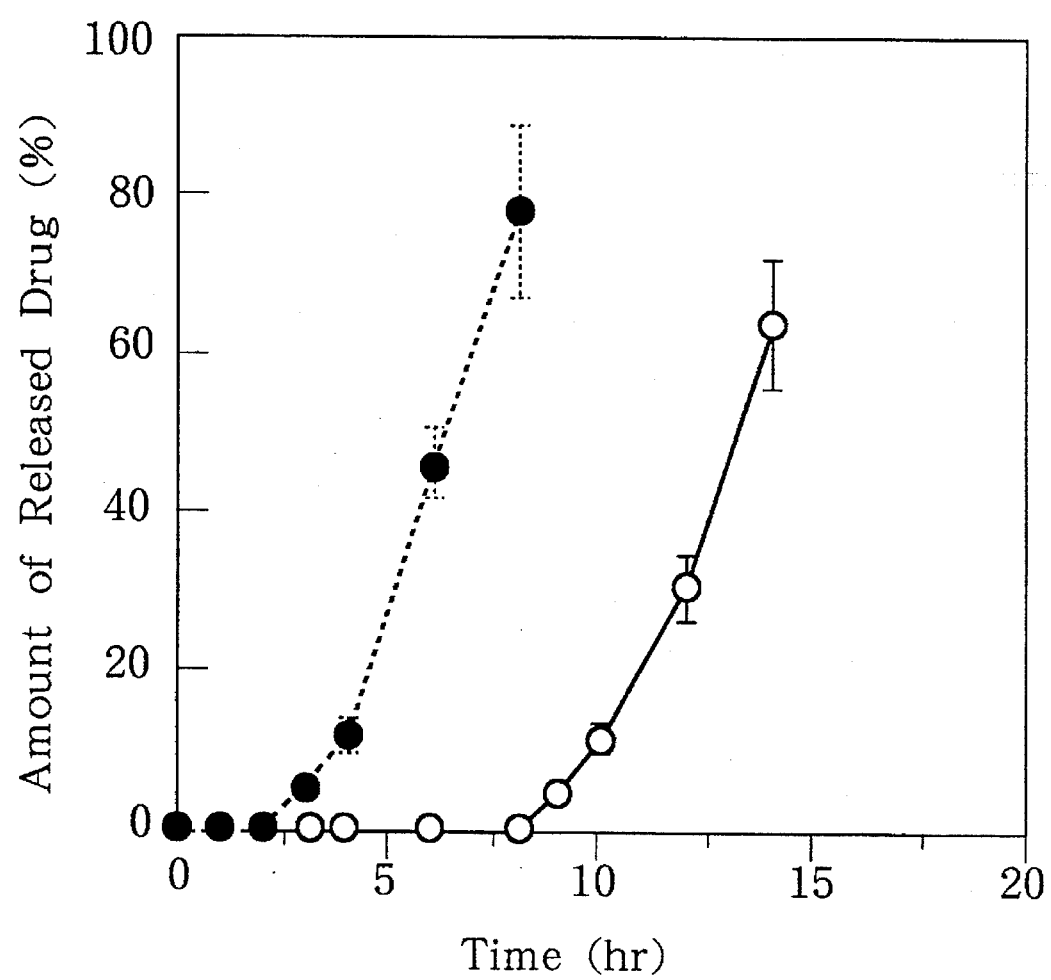
FIG. 1 is a graph showing the results of in vitro test on the release of drug.

The present invention will now be specifically described by referring to the following Examples.

EXAMPLE 1

A ketoprofen-containing solid drug was prepared according to the following formula:

| ketoprofen | 24.0 pt. by wt. |
| magnesium stearate | 1.0 pt. by wt. |
| lactose | 75.0 pt. by wt. |

Ketoprofen, lactose and magnesium stearate were mixed together to form a homogeneous mixture. This mixture was compressed with a tablet machine into tablets having a diameter of 7 mm and a weight of 210 mg. The obtained solid drug was coated as follows.

| | |
|---|---|
| Eudragit E (trade name) | 7.0 pt. by wt. |
| ethanol | 70.0 pt. by wt. |
| water | 19.5 pt. by wt. |
| talc | 3.5 pt. by wt. |

A solution comprising the above components was continuously sprayed at 50° C. on the solid drug preheated to 50° C. to form an inner coat. The weight increase of the solid drug was 30 mg.

After the completion of the spraying, the resulting drug was dried and further coated as follows.

| | |
|---|---|
| Eudragit S (trade name) | 7.0 pt. by wt. |
| ethanol | 70.0 pt. by wt. |
| water | 18.8 pt. by wt. |
| talc | 3.5 pt. by wt. |
| polyethylene glycol 6000 | 0.7 pt. by wt. |

A solution comprising the above components was continuously sprayed at 50° C. on the resulting drug preheated to 50° C. to form an outer coat. The weight increase of the solid drug was 20 mg.

Comparative Example 1

A ketoprofen-containing solid drug was prepared according to the following formula:

| | |
|---|---|
| ketoprofen | 24.0 pt. by wt. |
| magnesium stearate | 1.0 pt. by wt. |
| lactose | 75.0 pt. by wt. |

Ketoprofen, lactose and magnesium stearate were mixed together to form a homogeneous mixture. This mixture was compressed with a tablet machine into tablets having a diameter of 7 mm and a weight of 210 mg. The obtained solid drug was coated as follows.

| | |
|---|---|
| Eudragit S (trade name) | 7.0 pt. by wt. |
| ethanol | 70.0 pt. by wt. |
| water | 18.8 pt. by wt. |
| talc | 3.5 pt. by wt. |
| polyethylene glycol 6000 | 0.7 pt. by wt. |

A solution comprising the above components was continuously sprayed at room temperature on the solid drug preheated to 50° C. to form an inner coat. The weight increase of the solid drug was 30 mg. The resulting drug was dried and further coated as follows.

| | |
|---|---|
| hydroxypropylmethylcellulose | 4.0 pt. by wt. |
| polyethylene glycol 400 | 0.5 pt. by wt. |
| 95% ethanol | 85.5 pt. by wt. |
| water | 10.0 pt. by wt. |

Hydroxypropylcellulose was suspended in 95% ethanol, followed by the addition of a solution of polyethylene glycol 400. The obtained solution was sprayed on the above solid drug preheated to 50° C. to form an intermediate coat. The weight increase of the solid drug was 10 mg.

The resulting solid drug was furthermore coated by spraying a solution comprising the following components like in the formation of the above coat. The weight increase of the solid drug was 10 mg.

| | |
|---|---|
| Eudragit L100 (trade name) | 7.0 pt. by wt. |
| ethanol | 70.0 pt. by wt. |
| water | 18.8 pt. by wt. |
| talc | 3.5 pt. by wt. |
| polyethylene glycol 6000 | 0.7 pt. by wt. |

(A) In vitro test on the release of drug

The tablets prepared in Example 1 and Comparative Example 1 were examined for the release of ketoprofen. Each tablet was incubated in a buffer of pH2.0 for 2 hours, in a buffer of pH7.4 for 6 hours, and then in a cecal solution prepared by suspending the cecal contents in a phosphate buffer of pH7.4 containing 125 mg of glucose and 4.1 mg of benzyl viologen. The amount of the released ketoprofen was determined by liquid chromatography. The results are given in FIG. 1, wherein o represents the release pattern of the tablet prepared in Example 1 and, ● represents that of the tablet prepared in Comparative Example 1.

As apparent from the results of FIG. 1, the release of ketoprofen from the tablet prepared in Example 1 was observed specifically in a cecal solution, though it was not observed in a buffer of pH2.0 or 7.4 at all. On the other hand, most of the ketoprofen contained in the tablet prepared in Comparative Example 1 was released in a buffer of pH7.4.

(B) In vivo test on blood drug concentration

The tablet prepared in Example 1 was administered to a laboratory animal (beagle dog, male, weight: 10 kg) without anesthesia. The result is given in FIG. 2, wherein ● represents the result of the tablet of Example 1.

Figure 2:
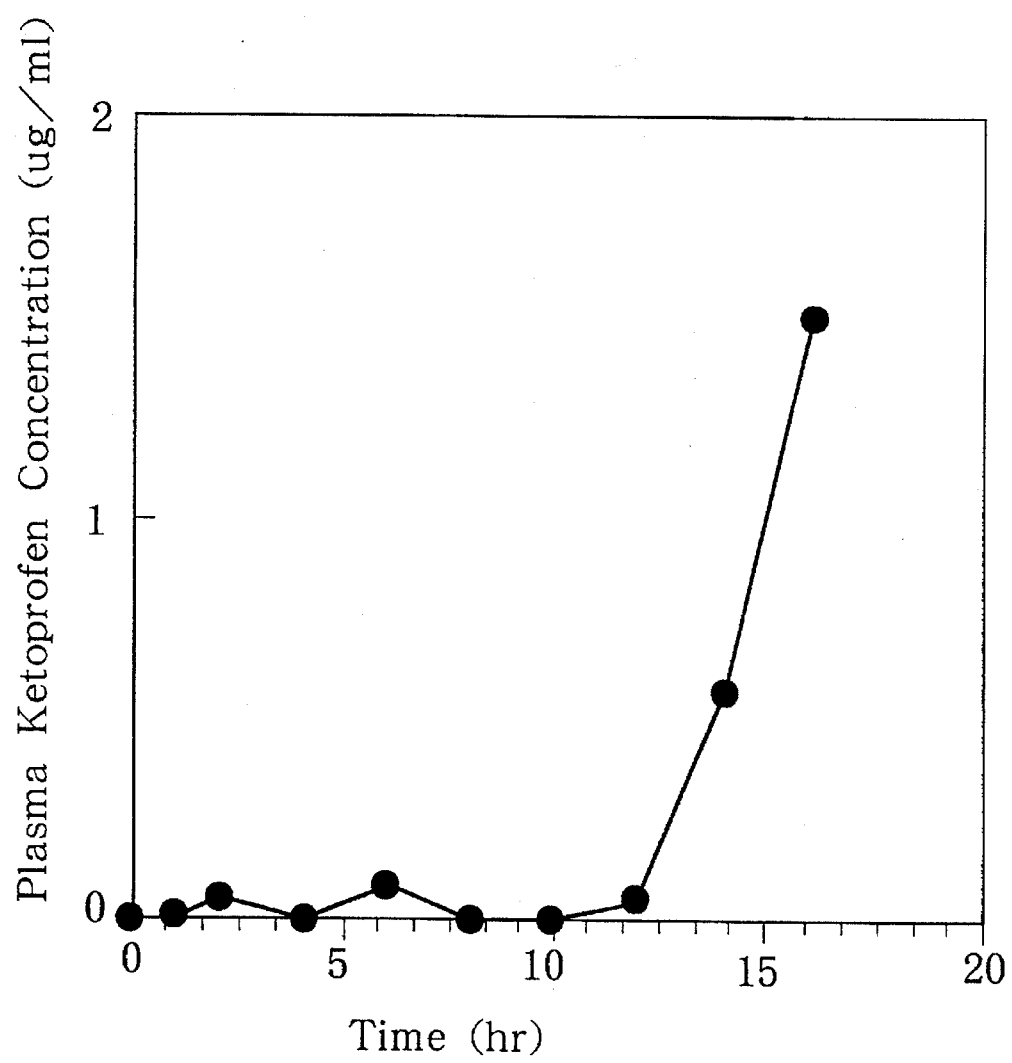
FIG. 2 is a graph showing the results of in vivo test on blood drug concentration.

As apparent from the result of FIG. 2, no ketoprofen was observed in the plasma in the early stages, though ketoprofen is very readily absorbable. After 14 hours and later, however, ketoprofen was observed in the plasma at extremely high concentrations.

EXAMPLE 2

Five kinds of tablets were prepared by repeating the same procedure as that of Example 1 except that the coating weights of the inner and outer coats were varied as specified in Table 1.

TABLE 1

| Sample No. | Coating wt. of Eudragit E (inner coat) | Coating wt. of Eudragit S (outer coat) |
|---|---|---|
| ① | 5% | 20% |
| ② | 20% | 20% |
| ③ | 40% | 20% |
| ④ | 20% | 5% |
| ⑤ | 20% | 40% |

*: each percentage is given by weight and based on the solid drug (C) In-vitro test on the influence of coating weight on the release of drug The tablets (Sample Nos. ① to ⑤) were tested for the release of ketoprofen. Each tablet was incubated in a buffer of pH7.4 for 4 hours and put in a cecal solution. The results of the test were given in FIG. 3, wherein o represents the result of Sample No. ①, ● represents the result of Sample No. ②, △ that of Sample No. ③, ▲ that of Sample No. ④ and o that of Sample No. ⑤.

Figure 3:
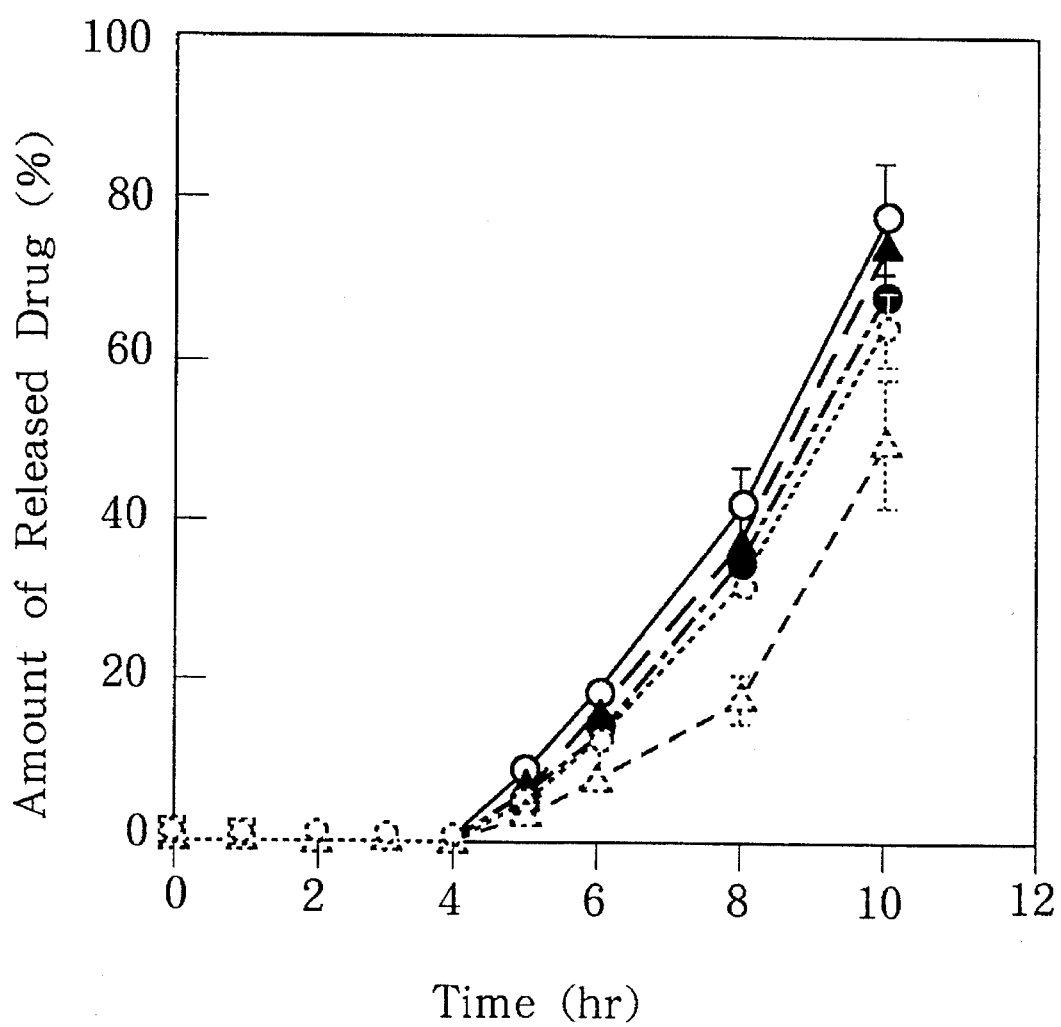
FIG. 3 is a graph showing the influence of coating weight on the release of drug in vitro.

As apparent from the results of FIG. 3, equivalent release patterns were exhibited even when the coating weight of Eudragit S (outer coat) was varied. On the other hand, when the coating weight of Eudragit E (inner coat) was varied, however, somewhat different release patterns were exhibited.

EXAMPLE 3

Ketoprofen-containing granules were prepared according to the following formula:

| | |
|---|---|
| ketoprofen | 20.0 pt. by wt. |
| lactose | 25.0 pt. by wt. |
| corn starch | 30.0 pt. by wt. |
| crystalline cellulose | 20.0 pt. by wt. |
| hydroxypropylcellulose | 5.0 pt. by wt. |

Ketoprofen, lactose, corn starch and crystalline cellulose were together mixed homogeneously, followed by the addition of a solution of hydroxypropylcellulose in purified water. The obtained mixture was kneaded and granulated with an extrusion granulator having a cylinder bore of 1 mm. The obtained granules were dried and subjected to size classification. The resulting granules were coated as follows to form an inner coat. The weight increase was 5 mg per 100 mg of the granules.

| | |
|---|---|
| Eudragit E (trade name) | 7.0 pt. by wt. |
| ethanol | 70.0 pt. by wt. |
| water | 19.5 pt. by wt. |
| talc | 3.5 pt. by wt. |

A solution comprising the above components was continuously sprayed on the granules preheated to 50° C. by the use of a flow coater at room temperature.

After the completion of the spraying, the resulting granules were dried and further coated with a solution comprising the following components to form an outer coat. The weight increase was 10 mg per 100 mg of the granules.

| | |
|---|---|
| Eudragit L (trade name) | 7.0 pt. by wt. |
| ethanol | 70.0 pt. by wt. |
| water | 18.8 pt. by wt. |
| talc | 3.5 pt. by wt. |
| polyethylene glycol 6000 | 0.7 pt. by wt. |

(D) Test on the influence of pH on the release of ketoprofen

This test was conducted in the same manner as that of Example 1. The results are given in FIG. 4, wherein o represents the release pattern at pH2.0, ● represents that at pH7.4, and Δ represents that exhibited when the granules were allowed to stand in a buffer of pH7.4 for 4 hours and put in a cecal solution.

Figure 4:
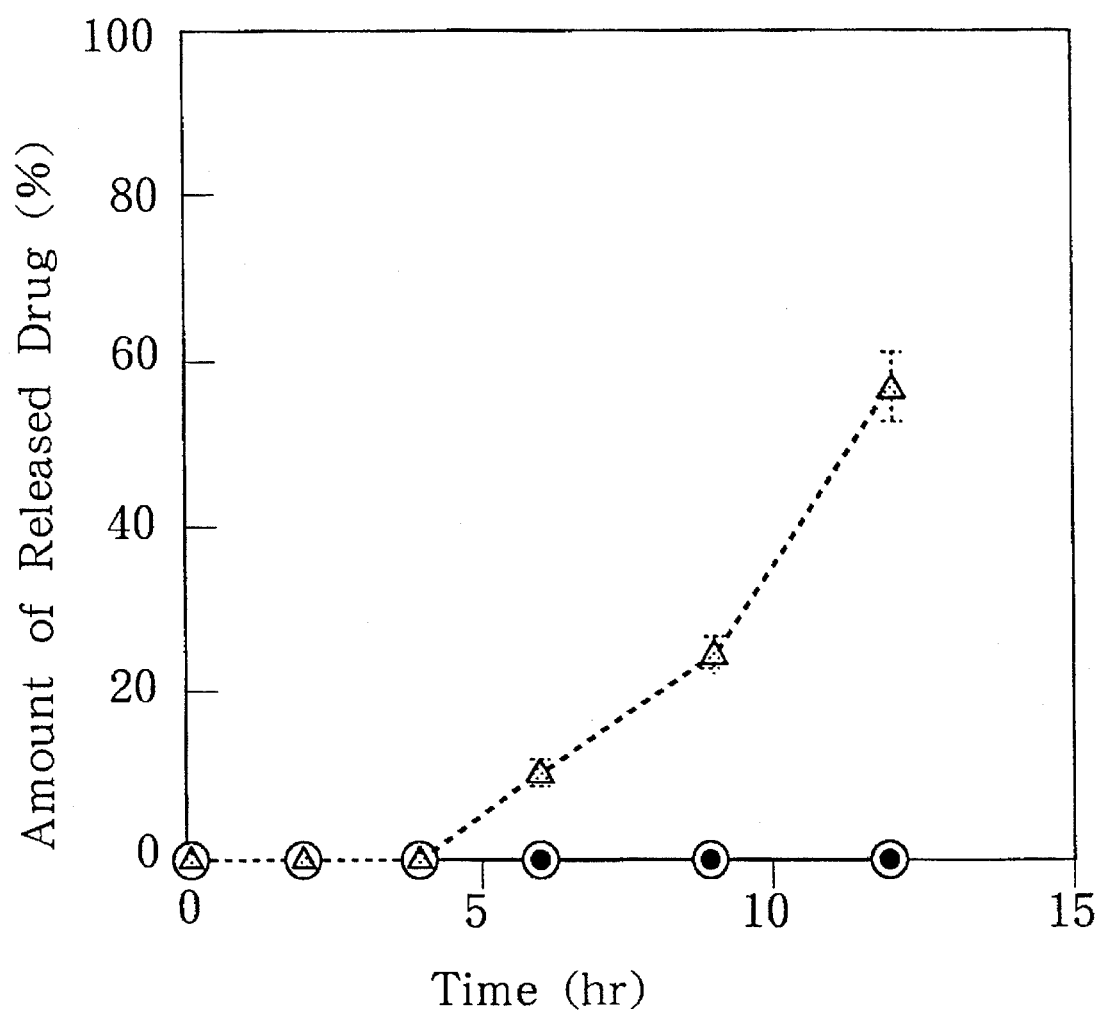
FIG. 4 is a graph showing the influence of pH on the release of ketoprofen.

As apparent from the results of FIG. 4, no ketoprofen was released at pH2.0 or pH7.4, while specific release of ketoprofen was observed only in a cecal solution.

EXAMPLE 4

A solid drug was prepared according to the following formula wherein fluorescein isothiocyanate dextran (hereinafter abbreviated to "FITC dextran") was used as a model compound having dissolution characteristics different from those of ketoprofen.

| | |
|---|---|
| FITC dextran | 2.5 pt. by wt. |
| magnesium stearate | 1.0 pt. by wt. |
| lactose | 96.4 pt. by wt. |
| carboxymethylcellulose | 0.1 pt. by wt. |

Both inner and outer coats were formed on the solid drug in the same manner as that of Example 1.

(E) Test on the influence of pH on the release of FITC dextran

This test was conducted in the same manner as that of Example 1. The results are given in FIG. 5, wherein o represents the release pattern at pH2.0, ● that at pH7.4, and ▲ represents that exhibited when the preparation was allowed to stand in a buffer of pH7.4 for 4 hours and put in a cecal solution.

Figure 5:
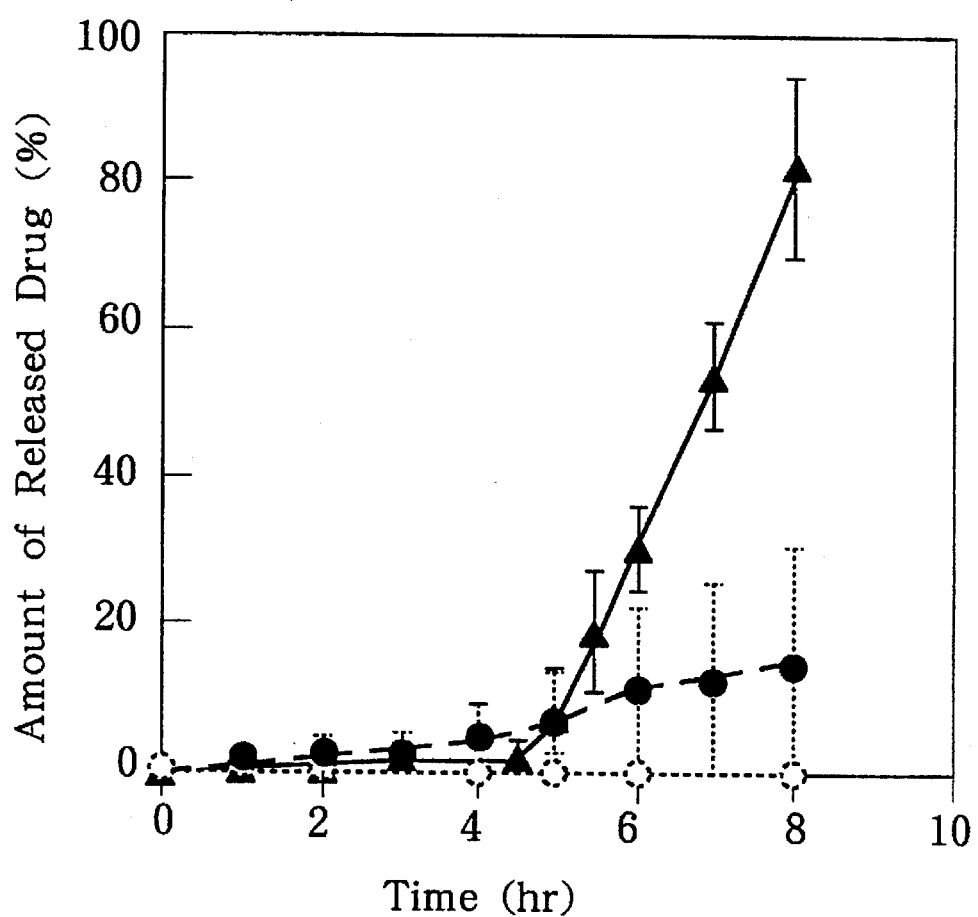
FIG. 5 is a graph showing the influence of pH on the release of FITC dextran.

As apparent from the results of FIG. 5, little FITC dextran was released in a buffer of pH2.0 or pH7.4, while rapid release of FITC dextran was observed in a cecal solution.

EXAMPLE 5

A solid drug having a calcitonin-containing core was prepared according to the following formula:

| | |
|---|---|
| calcitonin | 4.0 pt. by wt. |
| sucrose ester of fatty acid (F-160) | 5.0 pt. by wt. |
| magnesium stearate | 1.0 pt. by wt. |
| lactose | 90.0 pt. by wt. |

Calcitonin, lactose, magnesium stearate and sucrose ester of fatty acid were mixed together to form a homogeneous mixture. This mixture was compressed with a tablet machine into tablets having a diameter of 2 mm and a weight of 7 mg. The tablets were coated with a mixture comprising magnesium stearate (1 part by weight) and lactose (99 parts by weight). Both inner and outer coats were formed on the resulting tablets in the same manner as that of Example 1.

(F) Test on the influence of pH on the release of calcitonin

This test was conducted in the same manner as that of Example 1. The results are given in FIG. 6, wherein o represents the release pattern at pH2.0, ● represents that at pH7.4, and ▲ represents that exhibited when the tablet was allowed to stand in a buffer of pH7.4 for 4 hours and put in a cecal solution.

Figure 6:
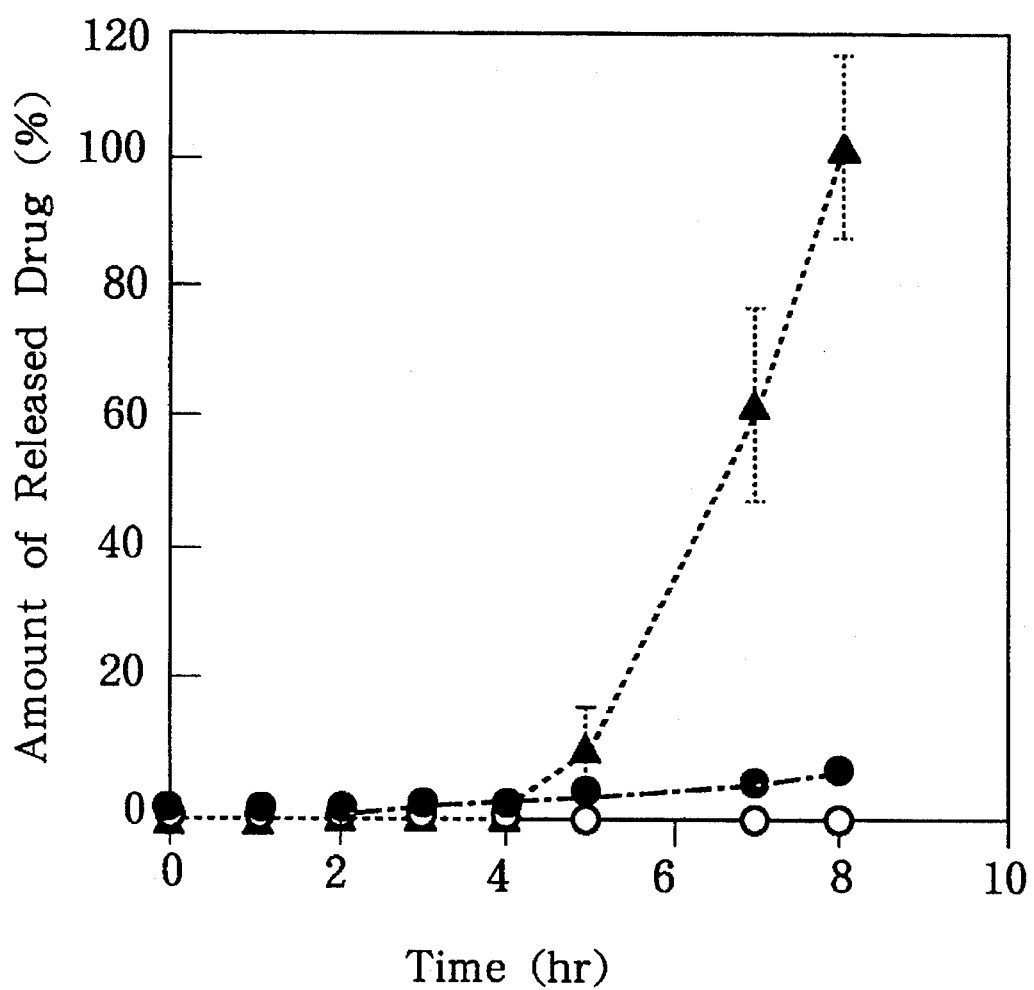
FIG. 6 is a graph showing the influence of pH on the release of calcitonin.

As apparent from the results of FIG. 6, little calcitonin was released in a buffer of pH2.0 or pH7.4, while rapid release of calcitonin was observed in a cecal solution.

(G) Blood calcium concentration test using dog

In a similar manner to that of Example 1, the tablet prepared in Example 5 was administered to dogs to determine the blood calcium concentration. The results are given in FIG. 7, wherein ● represents the result exhibited when the tablet of Example 5 was administered, and o represents the result exhibited when the tablet of Example 5 was not coated at all.

Figure 7:
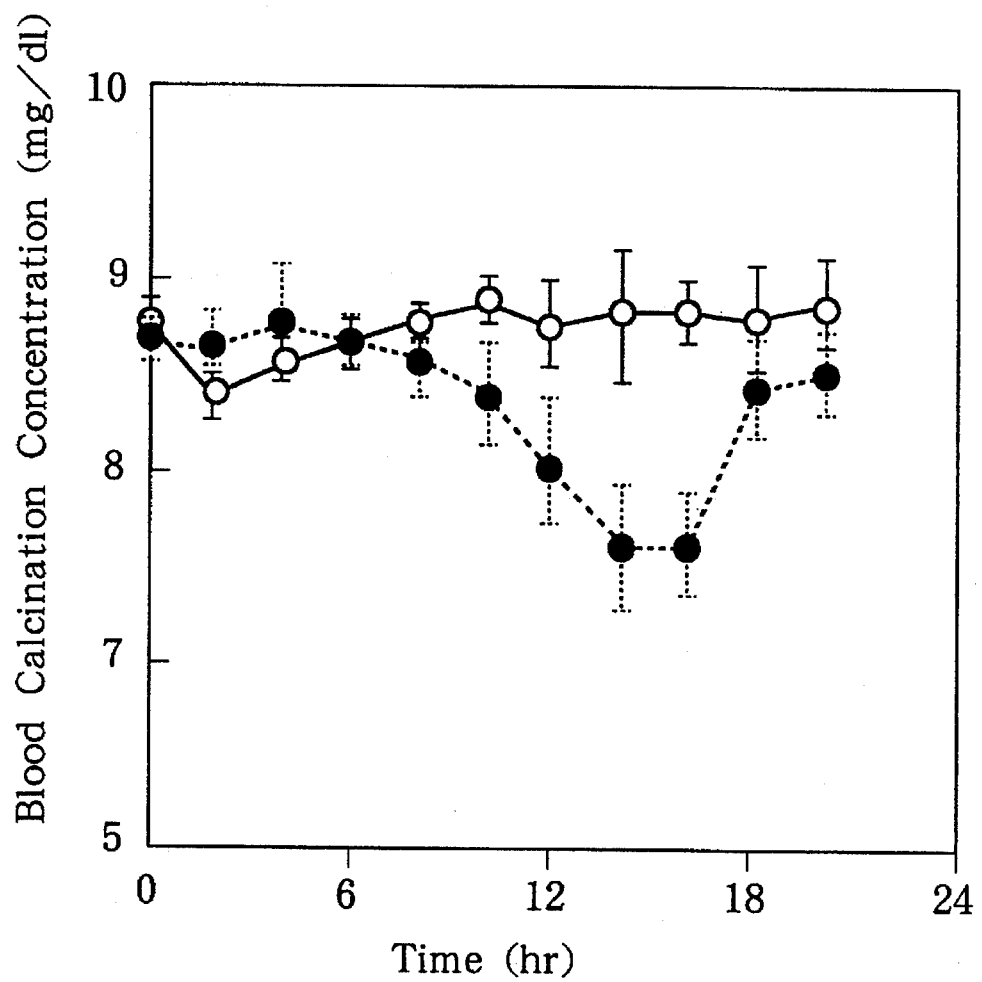
FIG. 7 is a graph showing the results of the blood calcium concentration test using dog.

As apparent from the results of FIG. 7, little lowering was observed in the blood calcium concentration, when the uncoated tablet was administered. On the other hand, lowering was observed in the blood calcium concentration 10 hours after the administration and later, when the double-coated tablet was administered.

EXAMPLE 6

Five kinds of tablets were prepared in a similar manner to that of Example 1 except that the coating weights of the inner and outer coats were varied as specified in Table 2.

TABLE 2

| Sample No. | Coating wt. of Eudragit E (inner coat) | Coating wt. of Eudragit S (outer coat) |
| --- | --- | --- |
| ① | 3% | 20% |
| ② | 5% | 20% |
| ③ | 7% | 20% |
| ④ | 5% | 5% |
| ⑤ | 5% | 3% |

*: each percentage is given by weight and based on the solid drug (H) In vitro test on the influence of coating weight on the release of drug These tablets were tested for the release of ketoprofen. Each tablet was incubated in a buffer of pH7.4 for 4 hours and put in a cecal solution. The results are given in FIG. 8, wherein ○ represents the result of Sample No. ①, ● represents that of Sample No. ②, Δ represents that of Sample No. ③, ▲ represents that of Sample No. ④, and □ represents that of Sample No. ⑤.

Figure 8:
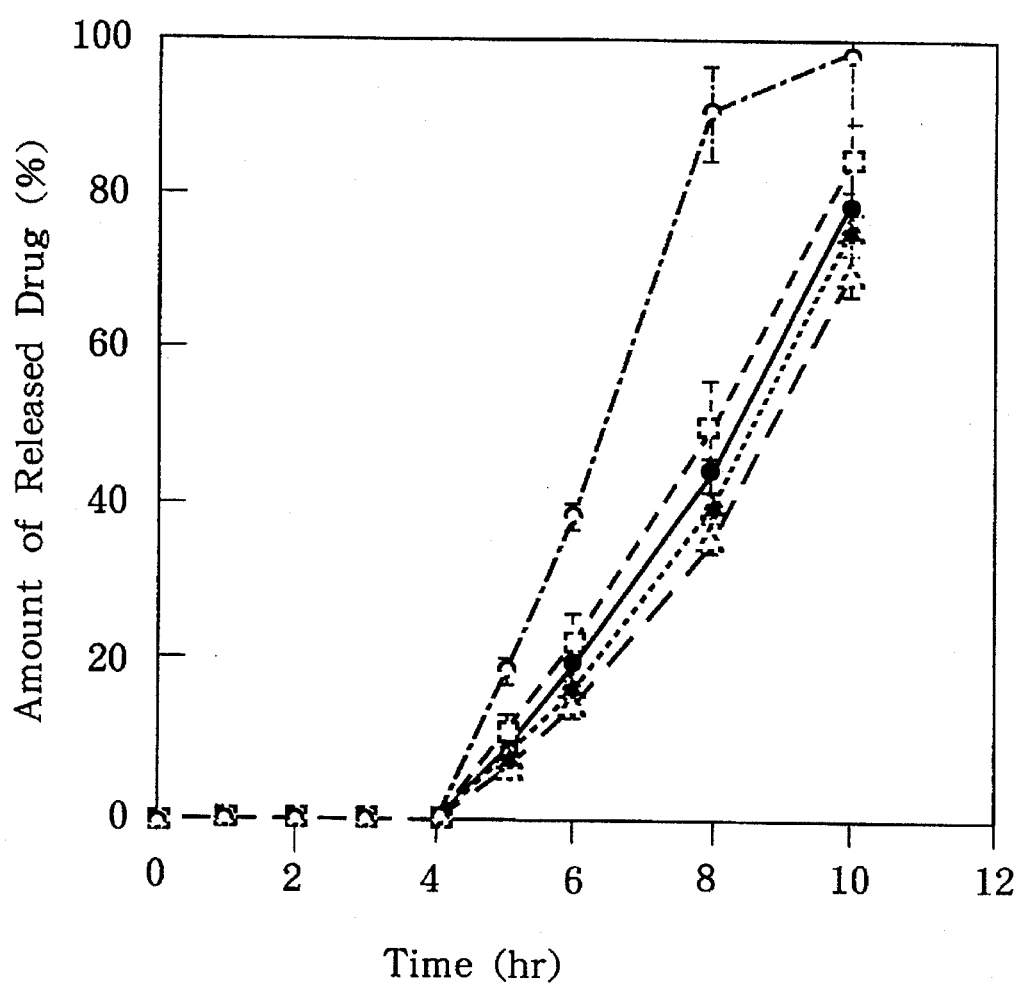
FIG. 8 is a graph showing the influence of coating weight on the release of drug in vitro.

As apparent from the results of FIG. 8, equivalent release patterns were exhibited, even when the coating weight of Eudragit S (outer coat) was varied. On the other hand, when the coating weight of Eudragit E (inner coat) was 5% by weight or below, excellent release patterns were exhibited.

EXAMPLE 7

Calcitonin-containing solid drugs were prepared according to the following formulae:

TABLE 3

| | Sample No. | | | | |
| --- | --- | --- | --- | --- | --- |
| | 1 | 2 | 3 | 4 | 5 |
| calcitonin | 0.28 mg | 0.28 mg | 0.28 mg | 0.28 mg | 0.28 mg |
| sucrose ester of fatty acid (F-160) | 25% | | | | |
| sodium caprate | | 25% | | 25% | |
| dipotassium glycyrrhizinate | | | 25% | 25% | |
| magnesium stearate | 1% | 1% | 1% | 1% | 1% |
| lactose | 74.0% | 74.0% | 74.0% | 49.0% | 99.0% |

*each percentage is given by weight

The components of each formula were mixed together to form a homogeneous mixture. This mixture was compressed into tablets having a diameter of 7 mm and a weight of 200 mg with a tablet machine. These tablets were each coated as follows.

| Eudragit E (trade name) | 7.0 pt. by wt. |
| --- | --- |
| ethanol | 70.0 pt. by wt. |
| water | 19.5 pt. by wt. |
| talc | 3.5 pt. by wt. |

A solution comprising the above components was continuously sprayed at 50° C. on the tablet preheated to 50° C. The weight increase of the solid drug was 14 mg. The resulting tablets were dried and further coated as follows.

| Eudragit S | 7.0 pt. by wt. |
| --- | --- |
| ethanol | 70.0 pt. by wt. |
| water | 18.8 pt. by wt. |
| talc | 3.5 pt. by wt. |
| polyethylene glycol 6000 | 0.7 pt. by wt. |

A solution comprising the above components was continuously sprayed at 50° C. on the tablets preheated to 50° C. The weight increase of the solid drug was 14 mg.

(I) In vivo test on the effect of sorbefacient

In a similar manner to that of Example 5, the tablets prepared in Example 7 were each administered to dogs to determine the blood calcium concentrations. The results are given in FIG. 9, wherein ○ represents the result of Sample No. ①, ● represents that of Sample No. ②, Δ represents that of Sample No. ③, ▲ represents that of Sample No. ④, and □ represents that of Sample No. ⑤.

Figure 9:
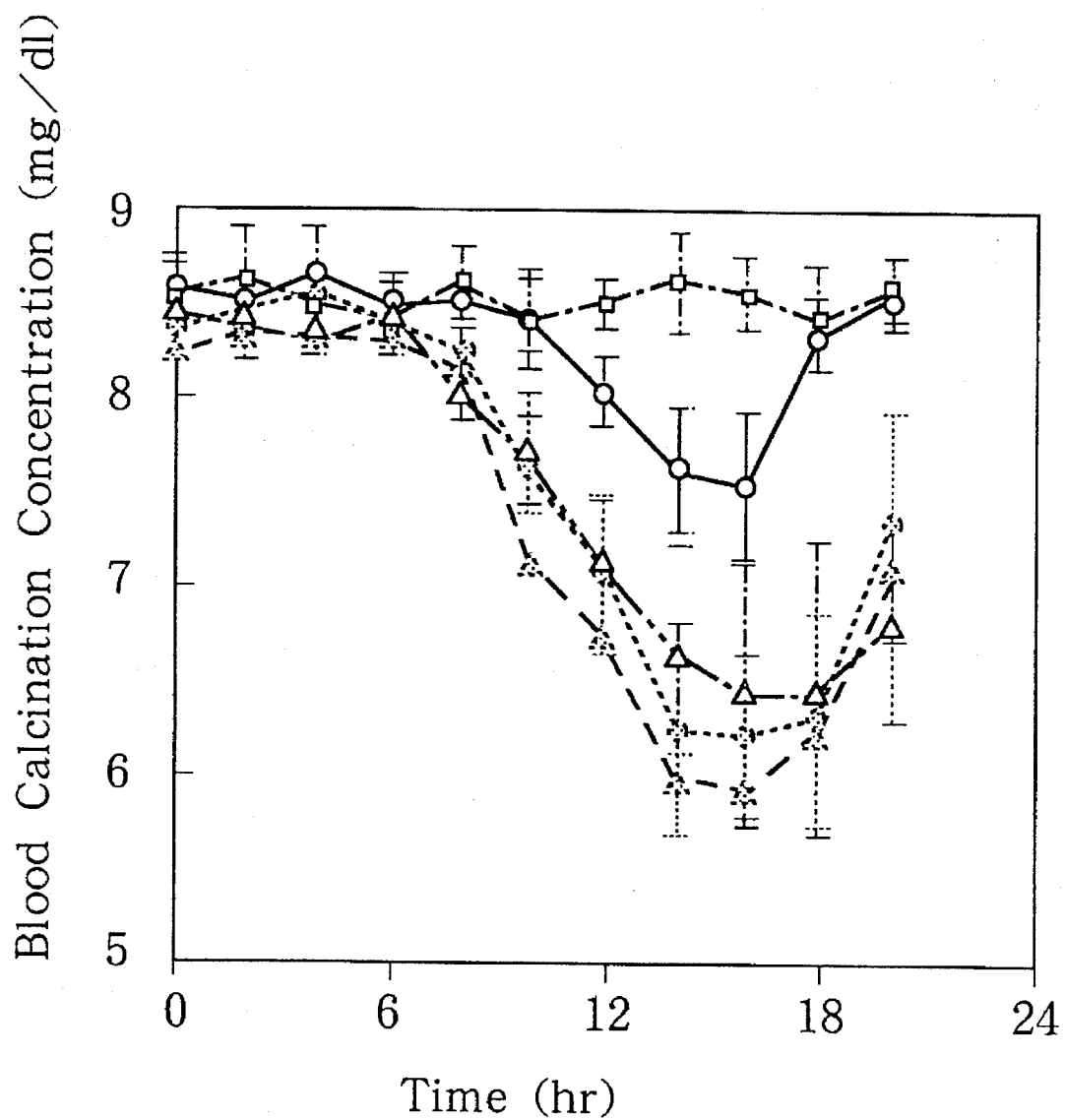
FIG. 9 is a graph showing the effect of sorbefacient in vivo.

As apparent from the results of FIG. 9, lowering in the blood calcium concentration was observed 10 hours after the administration and later when Sample No. ①, ②, ③ or ④ was administered, while no lowering was observed when Sample No. ⑤ not containing any sorbefacient was administered. Particularly excellent lowering in the blood calcium concentration was observed when sodium caprate or dipotassium glycyrrhizinate was used as the sorbefacient.

Industrial Applicability

The oral pharmaceutical preparation releasable in the lower digestive tract according to the present invention is characterized by the specific release of the active ingredient therefrom caused by the unique pH change in the digestive tract, so that the preparation little causes lowering or loss in the availability and scattering among individuals, though the preparation targetting the lower digestive tract (such as the large intestine) according to the prior art suffered from these disadvantageous phenomena.

In particular, the oral preparation of the present invention passes through the stomach and small intestine without being affected, and is disintegrated for the first time on arrival at the large intestine (i.e., the lower digestive tract) to release the active ingredient, which is then effectively absorbed in the large intestine to give a remarkably enhanced therapeutic effect and other excellent effects. Accordingly, the preparation of the present invention is useful as a pharmaceutical preparation for oral administration for treating a patient with a colonic or large intestine disease.

What is claimed is:

1. An oral pharmaceutical preparation releasable in the lower digestive tract, said preparation having a double-coated structure wherein a solid drug having a core containing an active ingredient is covered with both 1) an inner coat made of a cationic polymer which is soluble or swelling at a pH of 6.0 or below and 2) an outer coat made of an anionic polymer which is soluble at a pH of 5.5 or above, said cationic polymer being an aminoalkyl methacrylate copolymer, said anionic polymer being a methacrylic acid copolymer comprising methacrylic acid and methyl methacrylate.

2. The preparation according to claim 1 wherein said inner coat is applied to said solid drug to a thickness of 10–300 μm.

3. The preparation according to claim 1 wherein said inner coat is rendered smooth by addition of a plasticizer which is triacetin, a citrate ester or polyethylene glycol and includes a binding inhibitor which is a member selected from the group consisting of talc, titanium oxide, calcium phosphate, and hydrophobic anhydrous silicic acid.

4. The preparation according to claim 1 wherein said anionic polymer is applied in the amount of 1–40% by weight of said solid drug.

5. The preparation according to claim 1 wherein said drug is ketoprofen or calcitonin, said inner coat is made from dimethylaminoethyl methacrylate and said outer coat is made from 1) a copolymer comprising methacrylic acid and methyl methacrylate; or 2) hydroxy-propylcellulose.

6. The preparation according to claim 1, wherein the core contains a sorbefacient, said sorbefacient being a member selected from the group consisting of sugar esters, sucrose esters of fatty acid, glycyllysinate salts, glycyrrhetic acid, dipotassium glycyrrhizinate, bile acid, glycerol esters of fatty acid, 1-[(2-(decylthio)ethyl]azacyclopentan-2-one, adipic acid, basic amino acids, polyethylene glycol and sodium caprate.

7. The preparation according to claim 1 wherein the active ingredient is a member selected from the group consisting of peptides, proteins, anti-inflammatory agents, antineoplastic agents, antibiotics and chemotherapeutics.

* * * * *